(12) United States Patent
Ando

(10) Patent No.: US 6,945,929 B2
(45) Date of Patent: Sep. 20, 2005

(54) IMAGING DEVICE ASSEMBLY FOR ELECTRONIC STEREOSCOPIC ENDOSCOPE SYSTEM

(75) Inventor: Kunio Ando, Saitama (JP)

(73) Assignees: Fujinon Corporation, Saitama (JP); AI Systems Ltd., Saitama (JP)

(*) Notice: Subject to any disclaimer, the term of this patent is extended or adjusted under 35 U.S.C. 154(b) by 15 days.

(21) Appl. No.: 10/781,903

(22) Filed: Feb. 20, 2004

(65) Prior Publication Data

US 2004/0167378 A1 Aug. 26, 2004

(30) Foreign Application Priority Data

Feb. 21, 2003 (JP) ........................ 2003-044096

(51) Int. Cl.[7] ................. A61B 1/04; A61B 1/00; H04N 13/00
(52) U.S. Cl. .................. 600/111; 600/129; 348/45
(58) Field of Search ............. 600/109–111, 129–130, 600/166; 348/45, 76

(56) References Cited

U.S. PATENT DOCUMENTS 5,603,687 A * 2/1997 Hori et al. ............... 600/166
5,754,313 A * 5/1998 Pelchy et al. ............ 358/473
6,567,115 B1 * 5/2003 Miyashita et al. ........ 348/76

FOREIGN PATENT DOCUMENTS

JP 2000-199863 7/2000

* cited by examiner

Primary Examiner—John Leubecker
Assistant Examiner—Philip R Smith
(74) Attorney, Agent, or Firm—Snider & Associates; Ronald R. Snider

(57) ABSTRACT

An imaging device assembly for an electronic stereoscopic endoscope system comprises right and left solid state image pick-up modules set out side by side and right and left circuit boards with circuits formed thereon, respectively, that are connected to the right and left image pick-up modules, respectively. Each circuit board comprises a front section having a width approximately equal to a width of the solid state image pick-up module and a rear section broader than the front board section which is shaped to project laterally so as to overhang a rear section of the other circuit board and on which electronic parts incorporated in the circuit are mounted.

3 Claims, 3 Drawing Sheets

IMAGING DEVICE ASSEMBLY FOR ELECTRONIC STEREOSCOPIC ENDOSCOPE SYSTEM

BACKGROUND OF THE INVENTION

The application claims the priority of Japanese Patent Applications No. 2003-44096 filed on Feb. 21, 2003 which is incorporated herein by reference.

1. Field of the Invention

The present invention relates to an imaging device assembly for an electronic stereoscopic endoscope system, and, more specifically, to an imaging device assembly comprising a pair of, right and left, solid state image pickup devices that are dispose within a distal end of an insertion section of the endoscope together with a pair of, right and left, objective lens systems.

2. Description of the Related Art

An electronic stereoscopic imaging system for viewing three-dimensional images of an object fundamentally comprises an electronic endoscope for producing two optical images of an object, an electronic processing unit and a viewing system. The electronic endoscope includes a solid state imaging device comprising a pair of, namely right and left, image pick-up modules and right and left objective lens systems housed in a distal end barrel of the electronic endoscope. Each image pick-up module comprises a solid state image sensing element such as a charge coupled device (CCD) for producing a right or a left optical image of an object and converts the optical image into signals. The electronic processing unit processes the signals to generate right and left image signals and alternately provides the right and left image signals to the viewing system which includes a monitor unit and a viewing device such as specially-designed eyeglasses. The monitor unit displays alternating right and left video images corresponding to the alternately-provided right and left image signals on the screen. A properly-equipped viewer of the monitor screen will perceive three-dimensional video images of the object due to the repeatedly alternating left and right video images displayed on the monitor screen.

The solid state imaging device that is installed in the electronic endoscope for use with the electronic stereoscopic endoscope system is known in various forms, and may take any form well known in the art. Such a solid state imaging device disclosed, for example, in Japanese Unexamined Patent Publication No. 2000-199863 includes a circuit board and electronic parts that are disposed behind a solid state image sensing element, more specifically within an open space having the same cross-sectional area as the solid state image sensing element.

Meanwhile, in the recent years, solid state image sensing elements such as a CCD has made remarkable progress and it has turned to reality to provide $1/10$ inch microelectronic CCDs for commercial high technology equipments. Such a CCD is about the size of 2×2 mm and is fit to be incorporated as a solid state image sensing element of the image pick-up device in a slenderized electronic endoscope suitable for practical use.

One of the problems that occur in the case where the microelectronic CCDs are used for the imaging pick-up device of the electronic endoscope system is that it is hard to make the electronic endoscope sufficiently small in diameter in relation to sizes of associated electronic parts mounted together with the CCD. That is, in this type of solid state imaging device, it is general to mount resistors, transistors and other electronic parts forming a preamplifier that is connected directly to output terminals of the CCD on a circuit board connected to the CCD. The conventional CCD is large in size over against these resistors, transistors and other electronic parts and, in consequence, has no trouble in arranging these resistors, transistors and other electronic parts within an open space behind the CCD like the solid state imaging device disclosed in the above mentioned publication.

However, in the case where using these electronic parts including resisters and transistors, not custom-made parts but commercially available parts, for a preamplifier, it is hard to arrange these resistors, transistors and other parts orderly within the open space limited behind the $1/10$ inch CCD like the solid state imaging device disclosed in the above mentioned publication. This is because, while the $1/10$ inch CCD is about 2×2 mm, commercially available transistors measure 1.4×1.2×0.6 mm at the minimum, and commercially available 0.1 W resistors measure 1.6×0.8×0.3 mm at the minimum. Accordingly, as long as using commercially available electronic parts, the dimensional advantage of the microelectronic CCD must be surrendered in light of slenderizing the electronic stereoscopic endoscope.

SUMMARY OF THE INVENTION

It is therefore an object of the present invention to provide an imaging device assembly for an electronic stereoscopic endoscope system that, even though a microelectronic solid state image sensing element is used as image pick-up means, makes it possible to mount commercially available electronic parts to the imaging device assembly and, in consequence, is conducive to making an electronic endoscope with the imaging device assembly including the microelectronic solid state image sensing element slender.

The foregoing object of the present invention is achieved by an imaging device assembly that includes an imaging device that comprises a pair of solid state image pick-up modules set out side by side for converting right and left optical images of an object formed thereon, respectively, into right and left image signals, respectively, and a pair of circuit boards connected to the solid state image pick-up modules, respectively, each circuit board being equipped with a circuit and a group of electronic parts incorporated in the circuit. The circuit board comprises a front boarder section having a width approximately equal to a width of the solid state image pick-up module and connected to one of the solid state image pick-up modules at a front end thereof, and a rear board section formed as contiguously integral piece with the front board section and having a width greater than the front board section so as to project laterally from the front board section and thereby to overhang a space behind the other solid state image pick-up module. The group of electronic parts is fixedly mounted on the rear boarder section of the circuit board.

The circuit boards are connected to the top and bottom of the imaging device so as to be separated up and down from each other. In this configuration, the groups of electronic parts are attached to the circuit boards, respectively, so as to lie oppositely each other. Otherwise, the circuit boards may be connected to the imaging device at a half height position so as to be superposed on each other. In this configuration, the groups of electronic parts are attached to the circuit boards, respectively, so as to lie on opposite sides with respect to said circuit boards.

According to the imaging device assembly of the present invention, each of the right and left circuit boards that comprises a front board section having approximately the same width as the solid sate image pick-up module and a rear broader board section broader in width than the front board section is disposed within a tight space in the rear of and defined by the image pick-up module with wire leads of the image pick-up module connected to a circuit printed, or otherwise fixedly formed, on the circuit board. In other words, the circuit board is shaped to project laterally from the front board section so as to overhang a space in the rear of and defined by the counter image pick-up module, so that the right and left circuit boards overlap each other at the rear board sections within the space in the rear of and defined by the imaging device comprising the right and left image pick-up modules set out side by side. Accordingly, even when incorporating a microelectronic CCD in the image pick-up module, it is easy to mount conventional electronic parts, which are commercially available and comparatively large in size, on the circuit board without surrendering thinness of the electronic stereoscopic endoscope.

Furthermore, the right and left circuit boards with the electronic parts mounted thereon are separated up and down from each other so as to lie oppositely to each other between the right and left circuit boards or superposed on each other at a half height position of the imaging device so as to lie on opposite side with respect to the right and left circuit boards. This configuration makes it possible to lay out electronic parts efficiently in an available space on the circuit board. In consequence, the circuit boards including the electronic parts are entirely and orderly enclosed within the tight space in the rear and defined in width and height by the imaging device comprising the right and left image pick-up modules set out side by side.

BRIEF DESCRIPTION OF THE DRAWINGS

The above and other objects and features of the present invention will be clearly understood from the following detailed description when read with reference to the accompanying drawings, wherein the same numeral numbers have been used to denote same or similar parts or mechanisms throughout the drawings, and in which.

DETAILED DESCRIPTION OF THE PREFERRED EMBODIMENTS

In the following description, parts or units which are not of direct importance to the invention and parts or units which are purely of conventional construction will not be described in detail. For example, the objective lens systems for forming right and left optical images of an object on the imaging device, the electronic control system for providing video signals, etc., necessary to the electronic stereoscopic endoscope system in which the imaging device assembly of the present invention is installed, will not set out since their construction and operation can easily be arrived at by those skilled in the art.

Figure 1A:
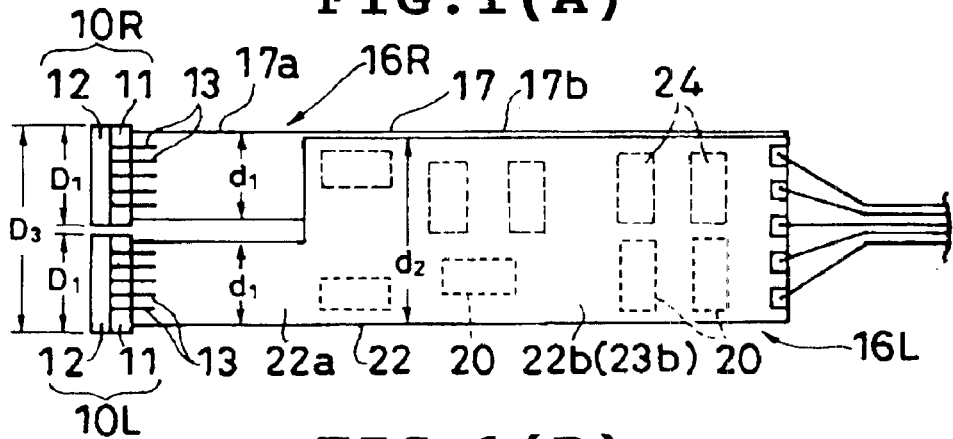
FIG. 1(A) is a plane view of an imaging device assembly for an electronic stereoscopic endoscope system according to a preferred embodiment of the present invention.
Figure 1B:
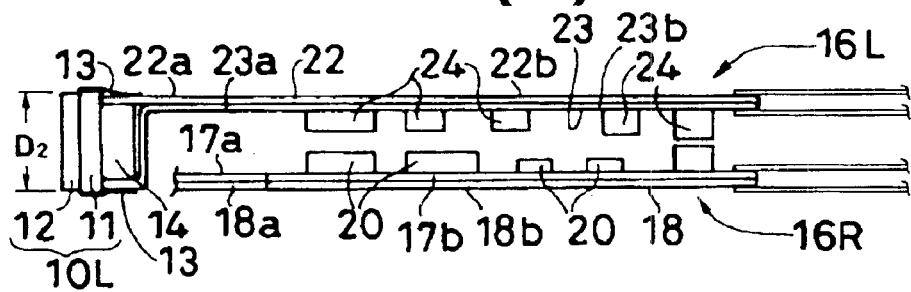
FIG. 1(B) is a side view of the imaging device assembly.
Figure 2:
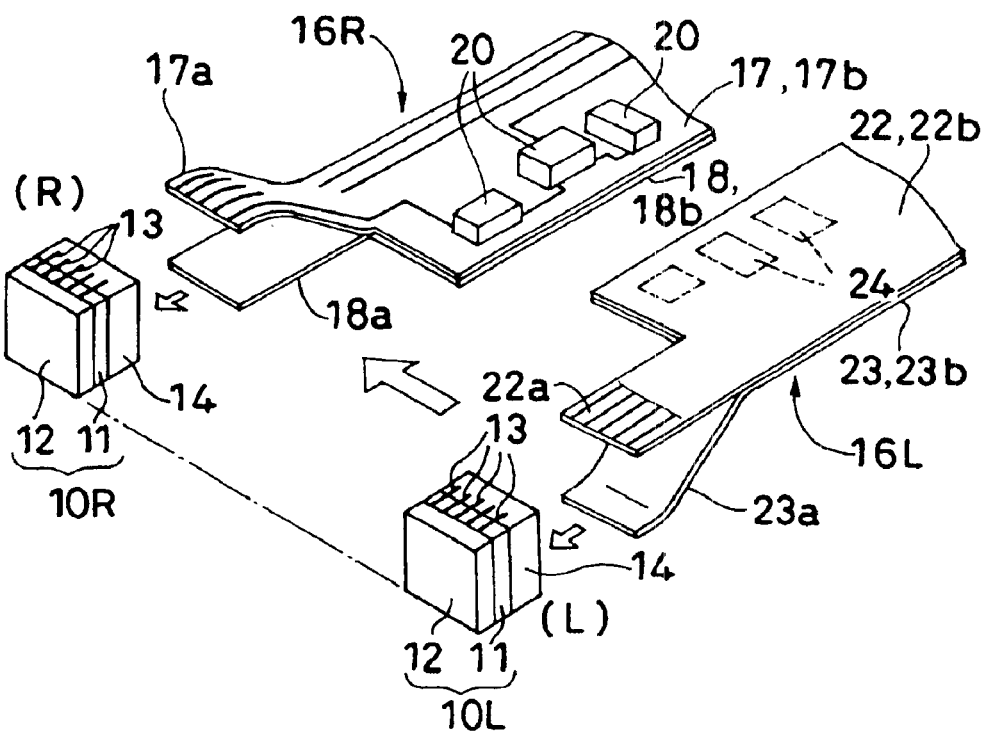
FIG. 2 is an exploded perspective view of the imaging device assembly.

Referring now to the drawings in detail and, in particular, FIGS. 1(A), 1(B) and 2 showing a structure of an imaging device assembly according to a preferred embodiment of the present invention that is used for an electronic endoscope of an electronic stereoscopic endoscope system, the imaging device assembly basically comprises right and left image pick-up modules 10R and 10L disposed side by side with a predetermined slight distance and right and left circuit boards 16R and 16L. The right and left image pick-up modules 10R and 10L are substantially identical in structure, size and operation. The right image pick-up module 10R includes a solid state image sensing element such as a CCD 11, a cover glass plate 12 that is substantially the same in size as the CCD 11 and adhered to a front face of the CCD 11, and a mounting block 14 that is substantially the same in size as the CCD 11 and adhered to a rear face of the CCD 11. The CCD 11 is provided with a number of wire leads 13 connected to CCD output terminals, respectively, and extending rearward across top and bottom faces of the CCD 11 and the mounting block 14. Similarly, the left image pick-up module 10L includes a solid state image sensing element such as a CCD 11, a cover glass plate 12 that is substantially the same in size as the CCD 11 and adhered to a front face of the CCD 11, and a mounting block 14 that is substantially the same in size as the CCD 11 and adhered to a rear face of the CCD 11. The CCD 11 is provided with a number of wire leads 13 connected to CCD output terminals, respectively, and extending rearward across top and bottom faces of the CCD 11 and the mounting block 14. The right and left image pick-up modules 10R and 11L are manufactured by a tape automated bonding (TAB) process. Although not shown in FIG. 1, right and left objective lens systems are disposed in front of the right and left image pick-up modules 10R and 10L, respectively, to produce right and left optical images of an object on image sensing surfaces of the right and left CCDs 11, respectively.

The right and left image pick-up module 10R and 10L are equipped with right and left circuit boards 16R and 16L, respectively, which are substantially identical in shape with each other and each of which comprises two, namely upper and lower circuit boards, flexible or rigid, overlapping each other. As will be described later, these upper and lower circuit boards that have given pattern of circuits printed, or otherwise formed, thereon, respectively, are adhered, or otherwise fixedly attached, to the mounting block 14 of the image pick-up module 10R, 10L so as to connect the wire leads 13 to the circuits.

As shown in FIG. 2, the right circuit board 16R comprises upper and lower circuit boards 17 and 18 on which given pattern of circuits and electronic parts are arranged as will be describe later. The upper circuit board 17 is divided into a front narrower board section 17a having a width d1 equal, or approximately equal, to a width D1 of the right image pick-up module 10R and a rear broader board section 17b having a width d2 greater than the width d1 of the front narrower board section 17a and, however, slightly smaller than an overall width D3 of the imaging device which comprises the right and left image pick-up modules 10R and 10L set out side by side at a predetermined slight distance as clearly shown in FIG. 1(A). That is, the upper circuit board 17 has a straight edge at one longitudinal side and is segmentized into parallel edges between the front narrower board section 17a and the rear broader board section 17b at another longitudinal side. Similarly, the lower circuit board 18 is divided into a front narrower board section 18a having the same width d1 as the front narrower board section 17a of the upper circuit board 17 and a rear broader board section 18b having the same width d2 as the rear broader board section 17b of the upper circuit board 17. These upper and lower circuit boards 17 and 18 are substantially identical in shape with each other, except that the front narrower board section 17a of the upper circuit board 17 is longer by a length substantially longer than the height D2 (see FIG. 1(B)) of the right image pick-up module 10R than the front narrower board section 18a of the lower circuit board 18.

On the other hand, the left circuit board 16L comprises upper and lower circuit boards 22 and 23 on which given pattern of circuits and electronic parts are arranged as will be describe later. The upper circuit board 22 is divided into a front narrower board section 22a having the same width d1 as the front narrower board section 17a of the upper circuit board 17 and a rear broader board section 22b having the said width d2 as the rear broader board section 17b of the upper circuit board 17. Similarly, the lower circuit board 23 is divided into a front narrower board section 23a having the same width d1 as the front narrower board section 22a of the upper circuit board 22 and a rear broader board section 23b having the same width d2 as the rear broader board section 22b of the upper circuit board 22. These upper and lower circuit boards 22 and 23 are substantially identical in shape with each other, except that the front narrower board section 23a of the lower circuit board 23 is longer by a length longer than the height D2 of the left image pick-up module 10L than the front narrower board section 22a of the upper circuit board 22.

Figure 3A:
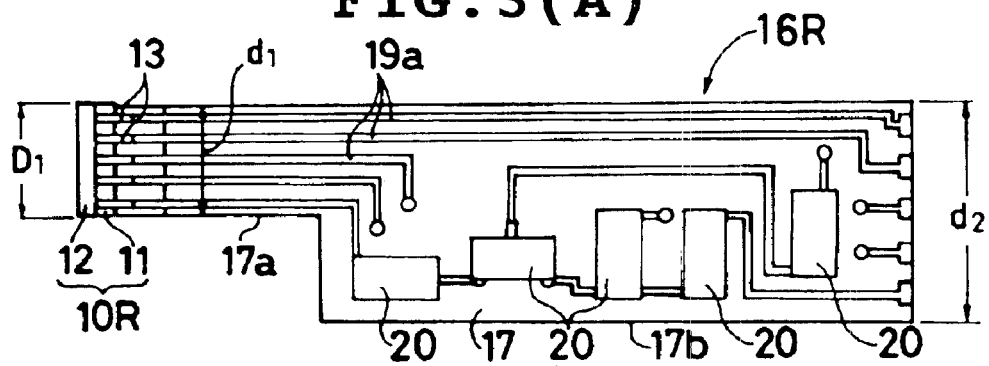
FIG. 3(A) is a plane view of a circuit connected to a right image pick-up module.
Figure 3B:
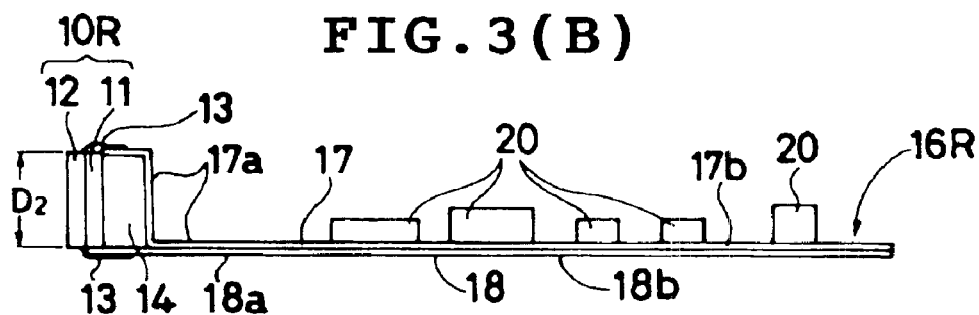
FIG. 3(B) is a side view of the circuit connected to the right image pick-up module.
Figure 3C:
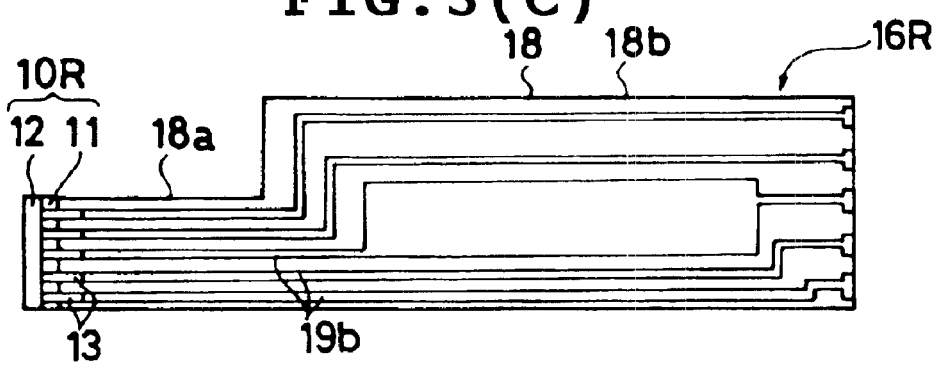
FIG. 3(C) is a bottom view of the circuit connected to the right image pick-up module.

As shown in FIGS. 3(A) to 3(C), the right circuit board 16R has given patterns of circuits and electronic parts. Specifically, as shown in FIG. 3(A), the right circuit board 16R has a given pattern of circuit 19a printed, or otherwise fixedly formed, on and extending across all over the tops of the front narrower and rear broader board sections 17a and 17b of the upper circuit board 17 and a group of electronic parts 20 fixedly attached to the top of the rear broader board section 17b of the upper circuit board 17. The electronic parts 20 include resistors, transistors, capacitors, etc. which are preferably arranged in a region of the rear broader board section 17b projecting laterally from the other longitudinal side of the front narrower board section 17a of the upper circuit board 17 and incorporated in the circuit 19a printed on the upper circuit board 17. The right circuit board 16R further has a given pattern of circuit 19b printed, or otherwise fixedly formed, on and extending across all over the reverses of the front narrower and rear broader board sections 18a and 18b of the lower circuit board 17 as shown in FIG. 3(C).

The lower circuit board 18 is generally not provided with any electronic part, differently from the upper circuit board 17, but provided with only wires partly laid thereon for electrically coupling the CCD 11 to an electronic processing module (not shown). In this event, the lower circuit board 18 may have the width d1 all the way along the length between the front and rear extremities.

Figure 3D:
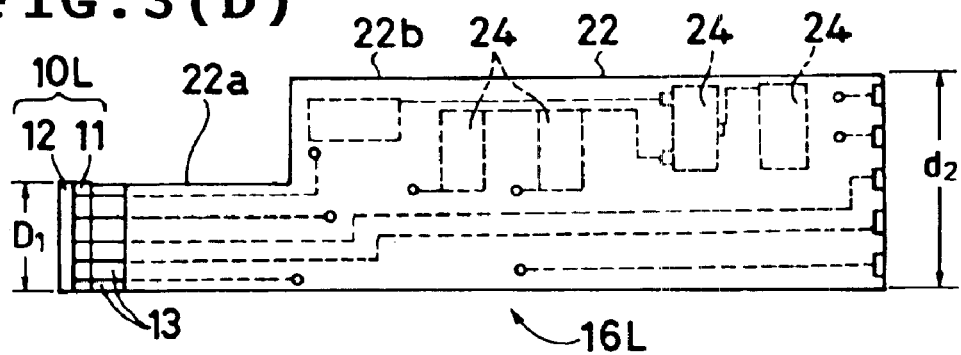
FIG. 3(D) is a plane view of a circuit connected to a left image pick-up module.

The left circuit board 16L has given patterns of circuits and electronic parts. Specifically, as shown in FIG. 3(D), the right circuit board 16L has a given pattern of circuit 21a printed, or otherwise fixedly formed, on and extending across all over the reverses of the front narrower and rear broader board sections 22a and 22b of the upper circuit board 22 and a group of electronic parts 24 fixedly attached to the reverse of the rear broader board section 22b of the upper circuit board 22. The electronic parts 24 include resistors, transistors, capacitors, etc. which are preferably arranged in a region of the rear broader board section 22b projecting laterally from the other longitudinal side of the front narrower board section 22a of the upper circuit board 22 and incorporated in the circuit 21a printed on the reverse of the upper circuit board 22. In FIG. 3(D), a circuit that is printed on the top of the upper circuit board 22 is omitted for the purpose of simplicity. The left circuit board 16L further has a given pattern of circuit (not shown) printed, or otherwise fixedly formed, on the reverse of the lower circuit board 23 and extending across all over the reverses of the front narrower and rear broader board sections 23a and 23b of the lower circuit board 23.

The lower circuit board 23 may have openings (not shown) formed in the rear broader board section 23b corresponding in position and size to the electronic parts 24 fixedly attached the rear broader board section 22b of the upper circuit board 22 so that the electronic parts 24 are received in the openings, respectively, so as thereby to prevent the electronic parts 24 from mechanically interferes with the lower circuit board 23 when the upper and lower circuit boards 22 and 23 are laid to overlap closely each other. Otherwise, in the event where the lower circuit board 23 is not provided with any electronic part but provided with only wires or a circuit partly laid thereon for electrically coupling the CCD 11 to an electronic processing module, the lower circuit board 23 may have the width d1 all the way along the length between the front and rear extremities.

The right circuit board 16R is connected to the right image pick-up module 10R in the following manner. As shown in FIG. 3(B), the front narrower board section 17a of the upper circuit board 17 is bent upward and forward to take a reverse L-shaped form at the front extremity so as thereby to be tightly fitted to a rear profile of the mounting block 14 of the left image pick-up module 10R and is connected to the right image pick-up module 10R by firmly adhering the reverse L-shaped end portion of the front narrower board section 17a of the upper circuit board 17 to the top and back surfaces of the mounting block 14. The lower circuit board 18 is connected to the right image pick-up module 10R by firmly adhering the straight end portion of the front narrower board section 18a of the lower circuit board 18 to the bottom surface of the mounting block 14. As shown in FIG. 3(A), the reverse L-shaped end portion of the front narrower board section 17a of the upper circuit board 17 extends to the top of the CCD 11 of the right image pick-up module 10R beyond the mounting block 14 so that the wire leads 13 of the CCD 11 are connected to the circuit 19a on the top of the upper circuit board 17. On the other hand, as shown in FIG. 3(C), the front end portion of the front narrower board section 18a of the lower circuit board 18 extends straight to the bottom of the CCD 11 of the right image pick-up module 10R beyond the mounting block 14 so that the wire leads 13 of the CCD 11 are connected to the circuit 19b on the reverse of the lower circuit board 18.

These upper and lower circuit boards 17 and 18 may be laid to overlap closely each other or may be adhered to each other at the rear broader board sections 17b and 18b.

The left circuit board 16L is connected to the left image pick-up module 10L in the following manner. As shown in FIG. 1(B), the front narrower board section 23a of the lower circuit board 23 is bent downward and forward to take an L-shaped form at the front extremity so as thereby to be tightly fitted to a rear profile of the mounting block 14 of the left image pick-up module 10L and is connected to the left image pick-up module 10L by firmly adhering the L-shaped end portion of the lower circuit board 23 to the bottom and back surfaces of the mounting block 14. The upper circuit board 22 is connected to the left image pick-up module 10L by firmly adhering the straight end portion of the front narrower board section 22a of the upper circuit board 22 to the top surface of the mounting block 14. The front end portion of the front narrower board section 22a of the upper circuit board 22 extends straight to the top of the CCD 11 of the left image pick-up module 10L beyond the mounting block 14 so that the wire leads 13 of the CCD 11 are connected to the circuit 21a on the reverse of the upper circuit board 22 as shown in FIG. 3(D). On the other hand, although not shown, the L-shaped end portion of the front narrower board section 23a of the lower circuit board 23 extends to the bottom of the CCD 11 of the left image pick-up module 10L beyond the mounting block 14 so that the wire leads 13 of the CCD 11 are connected to the circuit on the reverse of the lower circuit board 23.

The right and left image pick-up modules 10R and 10L with the right and left circuit boards 16R and 16L connected respectively thereto are mounted in the electronic endoscope in such a way that the right and left image pick-up modules 10R and 10L are arranged side by side on a level with each other leaving a predetermined slight distance between them. In this configuration, the right circuit board 16R extends approximately on a level with the bottom of the right image pick-up module 10R and the left circuit board 16L extends approximately on a level with the top of the left image pick-up module 10L. Therefore, the right and left circuit boards 16R and 16L are laid to overhang each other at their the rear broader board sections as shown in FIG. 1(A). As a result, both right and left circuit boards 16R and 16L are orderly enclosed within a tight space defined by and in the rear of the imaging device (with the same height D2 as the right and left image pick-up modules 10R and 10L and the overall width D3 of the imaging device that is twice as wide as the width D1 of the right and left image pick-up modules 10R and 10L). Furthermore, since clusters of the electronic parts 20 and 24 are arranged in the regions of the rear broader board sections 17b and 22b which project laterally in opposite directions from the front narrower board sections 17a and 22a of the upper circuit boards 17 and 22a, respectively, they are laid to separate laterally and vertically from each other, thereby being prevented from brushing each other.

In the case wherein flexible circuit boards are employed, it is preferable for the upper and lower flexible circuit boards 16R and 16L to have a width d2 slightly smaller than the overall width D3 of the imaging device and, however, they may have a width greater than the overall width D3 of the imaging device. Such the flexible circuit board can fall within the tight space in the rear of the imaging device by bending either or opposite side margins upward or downward.

According to the configuration of the imaging device assembly described above, the right and left circuit boards 16R and 16L with circuits printed thereon and electronic parts 20 and 24 are snugly enclosed within a tight space defined by and in the rear of the imaging device. In consequence, the electronic endscope is reduced in diameter as small as a diagonal distance of a rectangular contour of the imaging device having the overall width D3 and the height D2. Furthermore, since each of the right and left circuit boards 16R and 16L can have a width approximately twice as broad as the image pick-up module 10R, 10L, in particular the CCD 11, it is easy to lay commercially available electronic parts within a tight space in the rear of and defined by the CCD 11 even though a 1/10 inch microelectronic CCD is employed.

Figure 4:
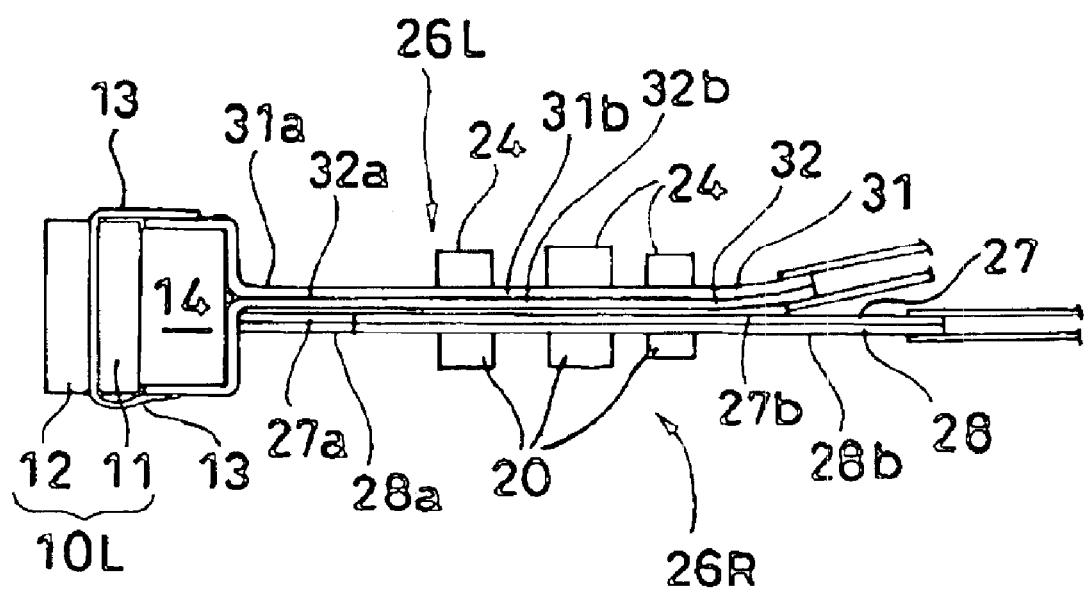
FIG. 4 is a side view of an imaging device assembly for an electronic stereoscopic endoscope system according to another preferred embodiment of the present invention.

FIG. 4 shows an imaging device assembly according to another preferred embodiment of the present invention for an electronic stereoscopic endoscope system in which right and left circuit boards are disposed in an intermediate position of an imaging device in an vertical direction. As shown, the imaging device assembly comprises right and left image pick-up modules (only the left image pick-up module 10L is shown) disposed side by side with a predetermined slight distance and right and left circuit boards 26R and 26L. The right and left image pick-up modules are substantially identical in structure, size and operation. The left image pick-up module 10L includes a solid state image sensing element such as a CCD 11, a cover glass plate 12 that is substantially the same in size as the CCD 11 and adhered to a front face of the CCD 11, a mounting block 14 that is substantially the same in size as the CCD 11 and adhered to a rear face of the CCD 11, and a number of wire leads 13 connected to CCD output terminals and extending across top and bottom faces of the CCD 11 and the mounting block 14. The right and left image pick-up modules are just the same in structure and size as those of the previous embodiment and need not be explained in more detail.

The left circuit board 26L, flexible or rigid, that is connected to the left image pick-up module 10L in an approximately half height position, and the right circuit board 26R, flexible or rigid, is connected to the right image pick-up module in an approximately half height position. These left and right circuit boards 26R and 26L are the same in size and structure as those of the previous embodiment. That is, the right circuit board 26R comprises upper and lower circuit boards 27 and 28 identical in shape with each other. The upper circuit board 27 is divided into a front narrower board section 27a having a width equal, or approximately equal, to a width of the CCD of the right image pick-up module and a rear broader board section 27b having a width greater than the width of the front narrower board section 27a but slightly smaller than an overall width of the imaging device comprising the right and left image pick-up modules arranged side by side at a predetermined slight distance. Similarly, the lower circuit board 28 is divided into a front narrower board section 28a having the same width as the front narrower board section 27a of the upper circuit board 27 and a rear broader board section 28b having the same width as the rear broader board section 27b of the upper circuit board 27. These upper and lower circuit boards 27 and 28 are separated from each other at the front narrower board sections 27a and 28a and, however, may or may not be adhered to each other at the rear broader board sections 27b and 28b.

The left circuit board 26L comprises upper and lower circuit boards 31 and 32 identical in shape with each other. The upper circuit board 31 is divided into a front narrower board section 31a having a width equal, or approximately equal, to a width of the CCD 11 of the left image pick-up module 10L and a rear broader board section 31b having a width greater than the width of the front narrower board section 31a but slightly smaller than an overall width of the imaging device. Similarly, the lower circuit board 32 is divided into a front narrower board section 32a having the same width as the front narrower board section 31a of the upper circuit board 31 and a rear broader board section 32b having the same width as the rear broader board section 31b of the upper circuit board 31. These upper and lower circuit boards 31 and 32 are separated from each other at the front narrower board sections 31a and 32a and, however, may or may not be adhered to each other at the rear broader board sections 31b and 32b.

The right circuit board 26R has a given pattern of circuit printed, or otherwise fixedly formed, on and extending across all over the tops and reverses of the front narrower and rear broader board sections 27a and 27b of the upper circuit board 27 and a group of electronic parts 20 fixedly attached to the reverse of the rear broader board section 27b of the upper circuit board 27 and incorporated in the circuit printed on the reverse of the upper circuit board 27. The electronic parts 20 are preferably arranged in a region of the rear broader board section 27b projecting laterally from the front narrower board section 27a of the upper circuit board 27 and incorporated in the circuit printed on the reverse of the upper circuit board 27. The right circuit board 26R further has a given pattern of circuit printed, or otherwise fixedly formed, on the reverse of the lower circuit board 28 and extending across all over the reverses of the front narrower and rear broader board sections 28a and 28b of the lower circuit board 28.

The lower circuit board 28 has openings formed in the rear broader board section 28b corresponding in position and size to the electronic parts 20 fixedly attached to the rear broader board section 27b of the upper circuit board 27 so that the electronic parts 20 are received in the openings, respectively, so as thereby to prevent the electronic parts 20 from mechanically interferes with the lower circuit board 28 when the upper and lower circuit boards 27 and 28 are laid to overlap closely each other.

On the other hand, the left circuit board 26L has a given pattern of circuit printed, or otherwise fixedly formed, on and extending across all over the tops of the front narrower and rear broader board sections 31a and 31b of the upper circuit board 31 and a group of electronic parts 24 fixedly attached to the top of the rear broader board section 31b of the upper circuit board 31 and incorporated in the circuit printed on the tip of the upper circuit board 31. The electronic parts 24 include resistors, transistors, capacitors, etc. which are preferably arranged in a region of the rear broader board section 31b projecting laterally from the front narrower board section 31a of the upper circuit board 31 and incorporated in the circuit printed on the upper circuit board 31. The left circuit board 26L further has a given pattern of circuit printed, or otherwise fixedly formed, on and extending across all over the reverses of the front narrower and rear broader board sections 32 of the lower circuit board 32.

In connecting the left circuit board 26L to the left image pick-up module 10L, the front narrower board section 31a of the upper circuit board 31 is bent upward and forward by a length approximately half the height of the left image pick-up module 10L to take a reverse L-shaped form at the front extremity so as thereby to be tightly fitted to a rear profile of the mounting block 14 of the left image pick-up module 10L. Similarly, the front narrower board section 32a of the lower circuit board 32 is bent downward and forward by a length approximately half the height of the left image pick-up module 10L to take an L-shaped form at the front extremity so as thereby to be tightly fitted to the rear profile of the mounting block 14 of the left image pick-up module 10L. The left circuit board 26L is connected to the left image pick-up module 10L by firmly adhering the reverse L-shaped end portion of the upper circuit board 31 to the top and back surfaces of the mounting block 14 and the L-shaped end portion of the lower circuit board 32 to the bottom and back surfaces of the mounting block 14 of the left image pick-up module 10L. The L-shaped end portions of the front narrower board sections 31a and 32a of the upper and lower circuit boards 31 and 32 extend to the top and the bottom of the CCD 11 of the left image pick-up module 10L, respectively, beyond the mounting block 14 so that the wire leads 13 of the CCD 11 are connected to the circuit on the top of the upper circuit board 31 and the circuit on the reverse of the lower circuit board 32. The right circuit board 26R is connected to the right image pick-up module in the same manner as applied to the left circuit board 26L described above. In this case, the left circuit board 26L is placed right above the right circuit board 26R so that the right and left circuit boards 26R and 26L overlap closely each other in a half height position of the imaging device.

According to the configuration of the imaging device assembly of the second embodiment, the right and left circuit boards 26R and 26L with circuits printed thereon and electronic parts 20 and 24 are snugly enclosed within a tight space defined by and in the rear of the imaging device. Further, the electronic parts are placed on opposite sides of the right and left circuit boards 26R and 26L, it is allowed to incorporate bulky electronic parts in the imaging device assembly.

Although the present invention has been described with reference to preferred embodiments thereof, it will be appreciated that variants and other embodiments can be effected by person of ordinary skill in the art without departing from the scope of the invention.

What is claimed is:

1. An imaging device assembly for an electronic stereoscopic endoscope system, said imaging device assembly including an imaging device that comprises a pair of solid state image pick-up modules set out side by side for converting right and left optical images of an object formed thereon, respectively, into right and left image signals, respectively, and a pair of circuit boards equipped with circuits, each of said circuit boards including a group of electronic parts incorporated therein and connected to said solid state image pick-up module, each of said circuit boards comprising:
   a front board section having a width approximately equal to a width of said solid state image pick-up module and being connected to one of said solid state image pick-up modules at a front end thereof; and
   a rear board section formed as contiguously integral piece with said front board section and having a width greater than said front board section so as to project laterally from said front board section and thereby to overhang a space behind the other of said solid state image pick-up module;
   wherein said group of electronic parts is fixedly mounted on said rear board section of each said circuit board.

2. An imaging device assembly for an electronic stereoscopic endoscope system as defined in claim 1, wherein said circuit boards are separated up and down from each other, and said groups of electronic parts are attached to said circuit boards, respectively, so as to lay oppositely each other.

3. An imaging device for an electronic stereoscopic endoscope system as defined in claim 1, wherein said circuit boards are superposed on each other at a half height position of said imaging device, and said groups of electronic parts are attached to said circuit boards, respectively, so as to lay on opposite side with respect to said circuit boards.

* * * * *